(12) United States Patent
Lin et al.

(10) Patent No.: US 7,790,651 B2
(45) Date of Patent: Sep. 7, 2010

(54) POROUS SILICA AND METAL OXIDE COMPOSITE-BASED CATALYSTS FOR CONVERSION OF FATTY ACIDS AND OILS TO BIODIESEL

(75) Inventors: Victor Shang-Yi Lin, Ames, IA (US); Jennifer A. Nieweg, Ames, IA (US); John G. Verkade, Ames, IA (US); Chinta Reddy Venkat Reddy, Ames, IA (US); Carla Kern, Ames, IA (US)

(73) Assignee: Iowa State University Research Foundation, Inc., Ames, IA (US)

( * ) Notice: Subject to any disclaimer, the term of this patent is extended or adjusted under 35 U.S.C. 154(b) by 806 days.

(21) Appl. No.: 11/506,417

(22) Filed: Aug. 18, 2006

(65) Prior Publication Data

US 2008/0021232 A1    Jan. 24, 2008

Related U.S. Application Data

(60) Provisional application No. 60/832,849, filed on Jul. 23, 2006.

(51) Int. Cl.
*B01J 21/06*    (2006.01)
*B01J 21/10*    (2006.01)
*C07C 51/43*    (2006.01)

(52) U.S. Cl. ............... 502/240; 502/60; 502/250; 502/251; 977/900; 554/174

(58) Field of Classification Search ........... 502/60, 502/240, 250, 251; 977/900; 554/174
See application file for complete search history.

(56) References Cited

U.S. PATENT DOCUMENTS

| | | | |
|---|---|---|---|
| 3,751,275 | A | 8/1973 | Oken |
| 5,134,242 | A | 7/1992 | Le et al. |
| 6,040,473 | A | 3/2000 | Knebel et al. |
| 6,204,424 | B1 | 3/2001 | Yadav et al. |
| 6,946,109 | B2 | 9/2005 | Pinnavaia et al. |
| 2009/0112007 | A1 | 4/2009 | Lin et al. |

FOREIGN PATENT DOCUMENTS

| | | |
|---|---|---|
| DE | 19602035 A1 | 7/1997 |
| EP | 1380637 A1 | 1/2004 |
| GB | 2269377 A | 2/1994 |
| WO | WO-2009058324 A1 | 5/2009 |

OTHER PUBLICATIONS

"International Application Serial No. PCT/US2008/012309, International Search Report mailed Feb. 18, 2009", 4 pgs.
"International Application Serial No. PCT/US2008/012309, Written Opinion mailed Feb. 18, 2009", 8 pgs.
Consolati, G., et al., "A positron annihilation study on the hydration of cement pastes", *Materials Chemistry and Physics*. 101, (2007), 264-268.
Ekolu, S. O, et al., "Pessimum effect of externally applied chlorides on expansion due to delayed ettringite formation: Proposed mechanism", *Cement and Concrete Research*, 36, (2006), 688-696.
Harbottle, M. J., et al., "Degradation of 2- chlorobenzoic acid in stabilised/solidified soil systems", *International Biodeterioration & Biodegradation*, 61 (2007), 173-181.
Ngamcharussrivichai, C., et al., "Modified Dolomites as Catalysts for Palm Kernel Oil Transesterification", *Journal of Molecular Catalysis A: Chemical*, 276, (2007), 24-33.
Svikle, D., et al., "Intensification of the estrification process of rosin", *Chemical Abstracts Service*, (1961), 261-261.
"International Search Report for corresponding PCT Application No. PCT/US06/32482", (May 23, 2007), 3 pgs.
"Written Opinion of the International Searching Authority for corresponding PCT Application No. PCT/IUS06/32482", (May 23, 2007), 4 pgs.
Bender, M., "Economic Feasibility Review for Community-Scale Farmer Cooperatives for Biodiesel", *Bioresource Technology*, 70, (1999),81-87.
Brunet, F., et al., "Application of $^{29}$Si Homonuclear and $^{1}$H-$^{29}$Si Heteronuclear NMR Correlation to Structural Studies of Calcium Silicate Hydrates", *J. Phys. Chem. B*., (2004), 15494-15502.
Chen, J. J., et al., "Solubility and Structure of Calcium Silicate Hydrate", *Cement and Concrete Research*, 34, (2004),1499-1519.
Clark, J. H., "Solid Acids for Green Chemistry", *Acc. Chem. Res*., 35, (2002),791-797.
Diasakou, M., et al., "Kinetics of the Non-Catalytic Transesterification of Soybean Oil", *Fuel*, 77(12), (1998),1297-1302.
Gryglewicz, S., "Alkaline-Earth Metal Compounds as Alcoholysis Catalysts for Ester Oils Synthesis", *Applied Catalysis A: General*, 192, (2000),23-28.
Gryglewicz, S., "Rapeseed Oil Methyl Esters Preparation Using Heterogeneous Catalysts", *Bioresource Technology*, 70, (1999),249-253.
Kiss, A. A., et al., "Solid Acid Catalysts for Biodiesel Production—Towards Sustainable Energy", *Adv, Synth. Catal*., 348, (2006),75-81.
Ma, F., et al., "Biodiesel Production: A Review", *Bioresource Technology*, 70, (1999),1-15.
Ogoshi, T., et al., "Soap and Related Products: Palm and Lauric Oil", *JAOCS*, 62(2), (1985),331-335.
Sohn, J. R., et al., "Acidic Properties of CaO—SiO$_2$ Binary Oxide Catalyst and Activity for Acid Catalysis", *Korean J. of Chem. Eng*., 14(3), (1997),192-197.
Suppes, G. J., et al., "Calcium Carbonate Catalyzed Alcoholysis of Fats and Oils", *JAOCS*, 78(2), (2001),139-145.
"International Application Serial No. PCT/US2008/012309, International Preliminary Report on Patentability mailed Jan. 13, 2010", 11 pgs.

*Primary Examiner*—Elizabeth D Wood
(74) *Attorney, Agent, or Firm*—Schwegman, Lundberg & Woessner, P.A.

(57) ABSTRACT

A recyclable esterification or transesterification catalyst and methods for making and using the same are provided herein. The catalyst can be used to prepare biodiesel or methyl soyate from various feedstocks, including vegetable oils and animal fats. The catalyst can both esterify free fatty acids and transesterify mono-, di-, and triglycerides. The catalyst can also be combined with a metal oxide, and optionally calcined, prior to carrying out a catalytic reaction.

18 Claims, 9 Drawing Sheets

(A)

(B)

POROUS SILICA AND METAL OXIDE COMPOSITE-BASED CATALYSTS FOR CONVERSION OF FATTY ACIDS AND OILS TO BIODIESEL

RELATED APPLICATIONS

This application claims priority under 35 U.S.C. §119(e) to U.S. Provisional Patent Application No. 60/832,849, filed Jul. 23, 2006, which application is incorporated herein by reference.

GOVERNMENT FUNDING

This invention was made with Government support of the United States Department of Agriculture Contract No. USDA/NRCS 68-3A75-3-146. The United States Government has certain rights in this invention.

BACKGROUND OF THE INVENTION

Biodiesel, such as soy diesel (methyl soyate), is becoming increasingly useful as a "green fuel". Biodiesel is a biodegradable and nontoxic alternative to diesel fuel. It is made from renewable biological sources such as vegetable oils and animal fats (*Bioresource Technology* 1999, 70, 1-15). Biodiesel fatty acid methyl esters have been recently accepted as a viable alternative to traditional petroleum-derived solvents, which are of environmental concern and are under legislative pressure to be replaced by biodegradable substitutes. Although interest in biodiesel is rapidly increasing, the process by which biodiesel is synthesized has not changed much in recent years.

Currently, soy diesel (methyl soyate) is made commercially by an energy and labor-intensive process wherein soybean oil is reacted with methanol at 140-150° F. (about 60-65° C.), often under pressure, in the presence of sodium methoxide to yield fatty acid methyl esters and glycerol. This process is called "transesterification". Isolation of the desired methyl soyate from the highly caustic (toxic) catalyst and other products, such as glycerol, involves a precise neutralization process with strong acids, such as hydrochloric acid (HCl), and extensive washes with water to remove the resulting sodium chloride (NaCl) salt. Also, the glycerol must be separated from the sodium chloride salt by vacuum distillation in an energy intensive operation for this high-boiling product (*Bioresource Technology* 1999, 70, 81; *Fuel* 1998, 77, 1297; *J. Am. Oil Chem. Soc.* 1985, 62, 331; *J. Am. Oil Chem. Soc.* 2001, 78, 139).

Researchers worldwide have been developing solid catalysts for the transesterification of oils to biodiesel. For example, various basic metal oxides, such as magnesium methoxide, calcium oxide, calcium alkoxide, and barium hydroxide (*Applied Catalysis, A: General* 2000, 192, (1), 23-28), have been demonstrated to be active catalysts for transesterification. However, the recyclability of these solid base catalysts is poor. This is because of the moderate solubility of some of these solid metal oxides and hydroxides in methanol (*Bioresource Technology* 1999, 70, (3), 249-253). Furthermore, these base catalysts are not suitable for feedstocks other than soybean oil, such as waste restaurant oils and rendered animal fats. The large amount (5-15 wt. %) of free fatty acids (FFAs) contained in these feedstocks significantly shortens the lifespan of base catalysts because of the saponification.

Currently, sulfuric acid, a homogeneous strong acid, is used as a pretreatment catalyst for converting FFAs to biodiesel. However, the need for neutralization before the transesterification reaction again creates economical and environmental concerns. While several solid acids, such as zeolite, ion-exchange resins, and sulfated zirconia, have been tested for FFA esterification (*Advanced Synthesis & Catalysis* 2006, 348, 75-81; *Accounts of Chemical Research* 2002, 35, (9), 791-797), it would be desirable to develop an integrated, acid-base cooperative system that can catalyze both esterification and transesterification reactions.

What is needed is a process for biodiesel production that does not require aqueous washes and neutralization steps, and a catalyst for that process that can be easily separated from the biodiesel products. An economical and recyclable catalyst for the conversion of oils to biodiesel is also needed. A catalyst that can economically catalyze both the esterification of free fatty acids and transesterify oils to biodiesel is further desired.

SUMMARY

The invention provides a porous silica-metal oxide composite-based catalyst that offers several advantages over known catalysts. The resulting catalysts are solids that function as heterogeneous catalysts that can be easily separated from a reaction mixture. The catalysts are easily recycled for use in subsequent catalytic reactions. The invention also provides a method to incorporate metal oxides into porous silica supports. The synthesis of the catalysts is significantly economical and commercially available resources are employed.

The catalyst is stable, even after repeated usage. The catalysts have very high surface areas due to their porosity. Additionally, the pores are sufficiently large to allow passage of vegetable and animal oils and alcohols used in the transesterification process. Furthermore, the pores can be chemically modified to allow more rapid passage of certain large molecules. The catalysts rapidly and under mild conditions convert vegetable and animal oils to ($C_{10}$-$C_{30}$)alkyl methyl esters and glycerin, which are easily mechanically separable. Glycerin has a variety of cosmetic and food uses, and is also under investigation as a biodegradable alternative to petroleum-based ethylene glycol and propylene glycol in aviation di-icing formulations.

Accordingly, the invention provides a recyclable esterification or transesterification catalyst comprising one or more porous particles that have a composite matrix of mesoporous silicates and alkaline earth metal oxides. The catalyst contains both acidic and basic sites and has a surface area of greater than about 50 $m^2$ per gram.

The invention also provides several methods of using the catalyst. The invention provides a method for transesterifying an ester to provide a ($C_1$-$C_4$)alkyl ester comprising: combining the ester, a ($C_1$-$C_4$)alcohol, and a catalyst of the invention under conditions wherein the catalyst catalyzes the formation of the ($C_1$-$C_4$)alkyl ester of the acid portion of the ester and the corresponding free alcohol of the ester.

The invention also provides a method for preparing fatty acid ($C_1$-$C_4$)alkyl esters from a feedstock that comprises one or more fatty acid glycerol esters and one or more fatty acids comprising: combining the feedstock, a ($C_1$-$C_4$)alcohol, and a catalyst of the invention under conditions wherein the catalyst catalyzes the formation of the corresponding fatty acid ($C_1$-$C_4$)alkyl esters.

The invention further provides a method for producing a fatty acid ($C_1$-$C_4$)alkyl ester comprising: combining a glyceride-containing vegetable or animal oil, a ($C_1$-$C_4$)alcohol, and a catalyst of the invention under conditions wherein the catalyst catalyzes formation of the corresponding fatty acid ($C_1$-$C_4$)alkyl ester and glycerol.

The invention also provides a method for preparing a fatty acid ($C_1$-$C_4$)alkyl ester from a fatty acid comprising: combining a fatty acid, a ($C_1$-$C_4$)alcohol, and a catalyst of the invention under conditions wherein the mesoporous silicate catalyzes formation of the corresponding fatty acid ($C_1$-$C_4$)alkyl ester.

Additionally, the invention provides a method for producing methyl soyate comprising: combining soybean oil, methanol, and a catalyst of the invention under conditions wherein the mesoporous silicate catalyzes formation of glycerol and the methyl soyate.

The invention also provides a method for preparing a mesoporous silicate alkaline earth metal oxide composite-based catalyst comprising:

a) combining a ($C_{10}$-$C_{24}$)alkyl-tri($C_1$-$C_3$)alkylammonium halide, a solvent, and a base, to form a first mixture;

b) heating the first mixture;

c) combining the first mixture with a tetra($C_1$-$C_4$)alkylorthosilicate and an alkali metal oxide or alkali metal hydroxide, to provide the catalyst in a second mixture; and d) recovering the catalyst from the second mixture.

DETAILED DESCRIPTION

The invention provides a new co-condensation method, which generates a series of mixed metal oxide mesoporous material that can effectively catalyze both the esterification of FFAs as well as the transesterification of an oil to biodiesel. The catalytic performance of three mesoporous calcium silicate (MCS) catalysts of varying calcium oxide content, a mesoporous magnesium silicate (MMS), and a mesoporous barium silicate (MBS) have been evaluated and described herein. By forming a mixed oxide from a strongly basic alkaline-earth metal oxide and a weakly acidic silica, it has been demonstrated that the acidity of silica can be significantly enhanced, thereby creating a cooperative acid-base mixed oxide catalyst. For example, in the case of calcium silicate mixed oxide, substituting Ca atoms with Si atoms at the high coordination environment (octahedral) of calcium oxide (strong base) sites create a 'positive' charge difference in comparison with the pure CaO material. Therefore, the silica sites of this type of mixed oxide materials are Lewis acidic, whereas the calcia sites are basic. The hydroxyl groups on the surface of the materials are also acidic and can be classified as Bronsted acids. Thus, these catalysts are able to efficiently facilitate the conversion of both vegetable oils and the higher FFA containing animal fats to biodiesel alkyl ester products.

The term "mesoporous particle" refers to a particle that is about 1 nm to about 50 nm in diameter, e.g., about 1 nm to about 20 nm in diameter.

Figure 8:
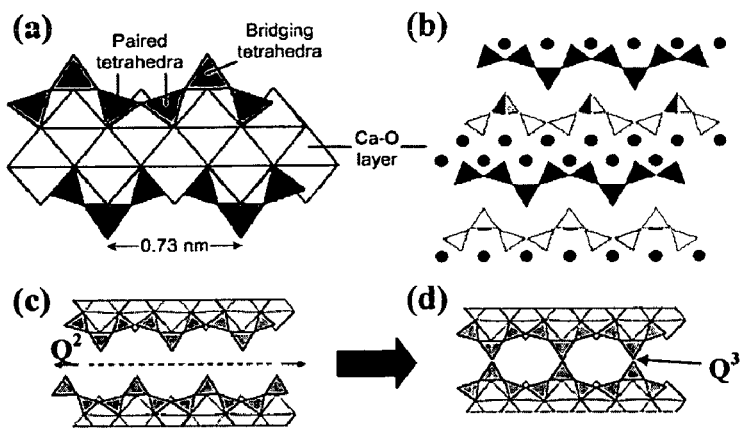
FIG. 8. Single layer of 1.4 nm tobermorite seen along (a) [210] illustrating the Ca—O main layer (light gray) with attached dreierketten (dark gray). (b) Layers of tobermorite in which a central Ca—O sheet is flanked on both sides by rows of single dreierketten, together with interlayer Ca atoms and water molecules. Water molecules and Ca atoms present in the interlayer spaces are omitted. Schematic representation of the difference in interlayer spacing of tobermorite between common calcium silicate hydrate gels (c) and an acid-base mixed oxide catalyst of the invention (d).

The term "composite matrix" refers to a matrix of silicon and oxygen atoms, wherein a portion of silicon atoms have been replaced by metal oxide atoms, and the coordination environment is a combination of at least tetrahedral and octahedral. A composite matrix can be illustrated as:

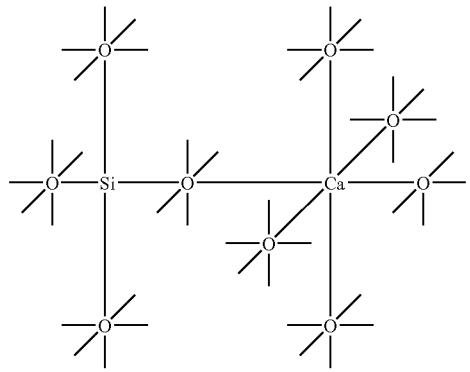

or as shown in FIG. 8.

The term "silicates" refers to a matrix of silicon and oxygen atoms, wherein the coordination environment is typically tetrahedral.

The term "alkaline earth metal" refers to beryllium (Be), magnesium (Mg), calcium (Ca), strontium (Sr), barium (Ba), and radium (Ra).

The term "alkaline earth metal oxide" refers to an oxide of an alkaline earth metal, including BeO, MgO, CaO, SrO, and BaO.

The term "alkaline earth metal hydroxide" refers to a hydroxide of an alkaline earth metal, including $Mg(OH)_2$, $Ca(OH)_2$, $Sr(OH)_2$, and $Ba(OH)_2$, and their various hydrated forms.

The term "bridging silicate tetrahedral" refers to layers of tobermorite as illustrated in FIG. 8(d).

The term "Q3-type silicon geometry" refers to a silicon atom with a chemical bonding environment of $Si(OSi)_3(OX)$, where X=H, Ca, or other alkaline earth metals. Such silicon geometry is further described by Brunet at al. in *J. Physical Chemistry B* 2004, 108, (40), 15,494-15,502, which is incorporated herein by reference.

The terms "to transesterify", "transesterifying", and "transesterification" refer to the alcoholysis of the glyceryl esters of a fat or oil with an alcohol, such as a $(C_1-C_4)$alkanol, to form newly formed esters and glycerol. The alkanol of the newly formed ester is derived from the alcohol used in the transesterification reaction. With respect to the transesterification of a mono-, di-, or triglyceride to provide the corresponding $(C_1-C_4)$alkyl ester and glycerol, the glycerol portion of the glyceride is preplaced by a $(C_1-C_4)$alcohol, thus liberating glycerol from the mono-, di-, or triglyceride. In biodiesel production, glycerol can be separated from biodiesel by gravitational settling, centrifugation, distillation, or combinations thereof.

The terms "ester", "$(C_1-C_4)$alkyl ester" and "fatty acid $(C_1-C_4)$alkyl ester" should be read in the context in which they are presented. One skilled in the art will readily recognize that the term "ester" will typically refer to the starting material ester, such as from a vegetable oil, an animal oil, or other feedstock oil, and the corresponding "$(C_1-C_4)$alkyl ester" refers to the product of a transesterification of the oil. Likewise, the term "fatty acid $(C_1-C_4)$alkyl ester" refers to a $(C_1-C_4)$alkyl ester of a starting material fatty acid or starting material fatty acid glyceryl ester.

Fatty acids can vary in carbon chain length and in the number of unsaturated bonds. Vegetable oils are typically made of a combination of fatty acids. Common vegetable oils include canola, coconut, corn, cottonseed, crambe, palm, peanut, rapeseed, soybean, and sunflower oils. These oils contain varying amounts of fatty acids, including combinations of $C_{16}-C_{24}$ fatty acids, typically with 0 to 3 sites of unsaturation in the carbon chain. Some examples of these fatty acids include lauric, myristic, palmitic, stearic, oleic, linoleic, and linolenic acids. Animal fats and oils are typically made of a combinations of fatty acids as well. Animal oils can be provided in various forms, including lard and tallow.

The term "acid portion of the ester" refers to the carboxyl (—C(=O)—O—) moiety of the ester.

The term "free alcohol of an/the ester" refers to the alkanol moiety of an ester after the alkanol portion has been hydrolyzed, alcoholyzed, or otherwise freed from the carboxyl moiety of the ester.

The term "$(C_1-C_4)$alcohol" or "$(C_1-C_4)$alkanol" refers to methanol, ethanol, propanol, iso-propanol, butanol, iso-butanol, sec-butanol, or a combination thereof.

The term "methyl soyate" refers to methyl esters of the fatty acids or fatty acid moieties in soybean oil.

The term "feedstock" refers to a large quantity, typically kilogram scale, of one or more fatty acid glycerol esters, one or more fatty acids, and optionally other substances. Feedstocks include vegetable oils and animal oils, such as animal fats and restaurant waste oils.

The term "fatty acid $(C_1-C_4)$alkyl ester" refers to a fatty acid that has been esterified with a $(C_1-C_4)$alkanol.

The term "glyceride-containing vegetable or animal oil" refers to a vegetable or animal oil that contains mono-, di-, or tri-esters of glycerol.

The term "$C_{10}-C_{24}$ fatty acid ester" refers to the ester of a $C_{10}-C_{24}$ fatty acid wherein the fatty acid portion of the molecule can be saturated or can have one or more sites of unsaturation, epoxidation, hydroxylation, or a combination thereof. For example, the fatty acid ester has 1, 2, 3, 4, or more sites of unsaturation, epoxidation, hydroxylation, or a combination thereof.

The terms "mono-, di-, or tri-ester of glycerol" refer to a glycerol molecule wherein one, two, or three hydroxyl groups of the glycerol have lost a hydrogen atom and have formed an ester linkage with an appropriate number of organic acids.

The Catalyst:

The catalyst is a esterification or transesterification catalyst comprising one or more porous particles that have a composite matrix of mesoporous silicates and alkaline earth metal oxides. The catalyst contains both acidic and basic sites and has a surface area of greater than about 50 m² per gram. The catalyst is preferably recyclable. The alkaline earth metal can be magnesium, calcium, or barium.

The catalyst can have a surface area of greater than about 50 m² per gram, greater than about 200 m² per gram, greater than about 400 m² per gram, or greater than about 800 m² per gram. In certain embodiments, the catalyst can have a surface area of about 200 to about 1,000 m² per gram. In other embodiments, the catalyst can have a surface area of about 250 to about 900 m² per gram. In certain specific embodiments, the catalyst has a surface area of about 250 to about 300 m² per gram, about 40 to about 500 m² per gram, or 800 to about 950 m² per gram.

The pores of the catalyst particle can be about 1 nm in diameter to about 20 nm in diameter. In certain embodiments, the pores of the particle are about 1 nm in diameter to about 10 nm in diameter. In certain specific embodiments, the pores of the particle are about 1 nm to about 2 nm in diameter, about 2 nm to about 3 nm, or about 8 nm to about 10 nm.

The silicate metal oxide catalyst can be made from a variety of ratios of silicon-containing starting materials and metal oxide-containing starting materials. The catalyst can have a silicon to alkaline earth metal ratio of about 0.1 to 1, to about 10 to 1. In other embodiments, the catalyst can have a silicon to alkaline earth metal ratio of about 1 to 1, to about 6 to 1. In still other embodiments, the catalyst has a silicon to alkaline earth metal ratio of about 1 to 1, to about 10 to 1. In various embodiments, the alkaline earth metal is calcium. In other embodiments, the alkaline earth metal is barium, or magnesium.

In one embodiment, the alkaline earth metal of the particle is calcium, bridging silicate tetrahedra are connected to form $Q^3$-type silicon atom geometry, and the catalyst exhibits spherical or sheet-like particle morphology with worm-like or channel-like mesopores. The spherical particles can have worm-like mesopores channel-like mesopores, or both. The sheet-like particles can also have worm-like mesopores channel-like mesopores, or both.

The silicon metal oxide composite catalyst can be used to catalyze a variety of esterification and transesterification reactions. The catalyst can be used in a method for transesterifying an ester to provide a $(C_1-C_4)$alkyl ester comprising: combining the ester, a $(C_1-C_4)$alcohol, and the catalyst under conditions wherein the catalyst catalyzes the formation of the ($C_1$-$C_4$)alkyl ester of the acid portion of the ester and the corresponding free alcohol of the ester.

The catalyst can be used in a method for preparing fatty acid ($C_1$-$C_4$)alkyl esters from a feedstock that comprises one or more fatty acid glycerol esters and one or more fatty acids comprising: combining the feedstock, a ($C_1$-$C_4$)alcohol, and the catalyst under conditions wherein the catalyst catalyzes the formation of the corresponding fatty acid ($C_1$-$C_4$)alkyl esters.

The catalyst can be used in a method for producing a fatty acid ($C_1$-$C_4$)alkyl ester comprising: combining a glyceride-containing vegetable or animal oil, a ($C_1$-$C_4$)alcohol, and the catalyst under conditions wherein the catalyst catalyzes formation of the corresponding fatty acid ($C_1$-$C_4$)alkyl ester and glycerol.

The catalyst can be used in a method for preparing a fatty acid ($C_1$-$C_4$)alkyl ester from a fatty acid comprising: combining a fatty acid, a ($C_1$-$C_4$)alcohol, and the catalyst under conditions wherein the mesoporous silicate catalyzes formation of the corresponding fatty acid ($C_1$-$C_4$)alkyl ester.

The catalyst can be used in a method for producing methyl soyate comprising: combining soybean oil, methanol, and the catalyst under conditions wherein the mesoporous silicate catalyzes formation of glycerol and the methyl soyate.

The ester can be a $C_{10}$-$C_{24}$ fatty acid ester. In another embodiment, the ester can be a $C_{16}$-$C_{24}$ fatty acid ester. The alkyl chain of the $C_{10}$-$C_{24}$ fatty acid ester or $C_{16}$-$C_{24}$ fatty acid ester can be saturated or it can have one or more sites of unsaturation or epoxidation. In another embodiment, the fatty acid ester has 1, 2, 3, or 4 sites of unsaturation, epoxidation, or a combination thereof.

Any variety of esters can be transesterified with the catalyst of the invention. The catalyst works well at transesterifying glyceride esters. The glyceride ester can be a mono-, di-, or tri-ester of glycerol. In one specific embodiment, the ester is a triglyceride.

Any variety of alcohols can be used to replace the alkanol portion of the ester that is transesterified. The alcohol is typically a ($C_1$-$C_4$)alcohol. The ($C_1$-$C_4$)alcohol can be methanol or ethanol. In other embodiments, the ($C_1$-$C_4$)alcohol can be propanol, iso-propanol, butanol, iso-butanol, sec-butanol, or a combination thereof.

The esterification or transesterification can be carried out under mild conditions. The formation of the ester can be carried out at a temperature of less than about 100° C. In another embodiment, the formation of the ester can be carried out at a temperature of less than about 90° C. In other embodiments, the formation of the ester can be carried out at a temperature of about 20° C. to about 100° C. In yet another embodiment, the formation of the ester can be carried out at a temperature of about 30° C. to about 90° C., about 40° C. to about 85° C., or about 50° C. to about 80° C.

One advantage of the catalyst described herein is that besides the alcohol used to esterify or transesterify a compound, no other solvent is required. Thus, the formation of the product ester can be carried out without added solvent. In other embodiments, an organic solvent can be added to alter the solubility, viscosity, or other properties of the starting oil. Such solvents include ethereal solvents such as ethyl ether, tetrahydrofuran, or dioxane; hydrocarbon solvents such as pentane or hexane; ketones such as acetone or t-butyl methyl ketone; or a combination thereof.

In another embodiment, the mesoporous silicate alkaline earth metal oxide composite-based catalyst can be combined with metal oxide particles prior to carrying out an esterification, transesterification, or other biodiesel production reaction. The metal oxide particles can be magnesium oxide particles, calcium oxide particles, barium oxide particles, or a combination thereof. The composite-based catalyst can be calicined (e.g., heated to above about 100° C., or to about 500° C. to about 600° C.) before being combined with metal oxide particles, or the composite-based catalyst can be calcined together with the metal oxide particles.

Methods of Making the Catalyst:

A method for preparing a mesoporous silicate alkaline earth metal oxide composite-based catalysts is provided herein. The method includes:

a) combining a ($C_{10}$-$C_{24}$)alkyl-tri($C_1$-$C_3$)alkylammonium halide, a solvent, and a base, to form a first mixture;

b) heating the first mixture;

c) combining the first mixture with a tetra($C_1$-$C_4$)alkylorthosilicate and an alkali metal oxide or alkali metal hydroxide, to provide the catalyst in a second mixture; and d) recovering the catalyst from the second mixture.

The method can include heating or calcinating the catalyst recovered from the second mixture. For example, the recovered catalyst can be heated to greater than about 100° C., to greater than about 250° C., to greater than about 400° C., to greater than about 500° C., to greater than about 600° C., or to greater than about 700° C. The recovered catalyst can be heated to about 100° C. to about 700° C., or to about 150° C. to about 700° C. In other embodiments, the recovered catalyst is heated to about 450° C. to about 650° C., or to about 500° C. to about 600° C.

A variety of tetraalkyl ammonium compounds can be used to prepare the catalysts. The ($C_{10}$-$C_{24}$)alkyl-tri($C_1$-$C_3$)alkylammonium halide can be a ($C_{10}$-$C_{24}$)alkyl-trimethylammonium halide. The tri($C_1$-$C_3$)alkyl groups can be methyl, ethyl, or propyl groups. The ($C_{10}$-$C_{24}$)alkyl-tri($C_1$-$C_3$)alkylammonium halide can be a cetyltrimethylammonium halide. The halide can be chloride, bromide, iodide, or a combination thereof.

The solvent used to prepare the catalysts can be water. The solvent can also be a 'solvent system' wherein one or more other solvents are added to the water to alter or modify the properties of the particles prepared.

The base used to prepare the catalysts can be an alkali metal hydroxide. For example, the base can be lithium hydroxide, sodium hydroxide, potassium hydroxide, or a combination thereof.

In preparing the first mixture in the catalyst preparation, heating is often advantageous. The first mixture can be heated to greater than about 30° C., greater than about 50° C., greater than about 60° C., or greater than about 75° C. The first mixture can be heated to about 60° C. to about 100° C., about 70° C. to about 90° C., or to about 80° C.

The silicate template of the catalyst particles can be prepared from a variety of orthosilicates. In one embodiment, the tetra($C_1$-$C_4$)alkylorthosilicate is tetraethylorthosilicate. In other embodiments, other orthosilicates can be employed, such as tetramethylorthosilicate or other related materials.

The alkali metal oxide used to prepare the catalyst particle can be MgO, CaO, or BaO. The alkali metal hydroxide used to prepare the catalyst particle can be Mg(OH)$_2$ or Ca(OH)$_2$.

As described above, the catalyst contains both acidic and basic sites. The acidic sites can be Lewis acidic or Bronsted acidic. The basic sites can be Lewis basic or Bronsted basic.

After the catalyst is prepared, the particles can be recovered from the reaction mixture by a variety of techniques, including decanting or filtering, such as through a sintered glass funnel. The catalyst can maintain catalytic activity after more than five times of using and recovering the catalyst. In certain embodiments, the can maintain catalytic activity after more than ten times, or more than twenty times of using and recovering the catalyst.

For example, the preparation of mesoporous metal oxide silicate catalysts can be prepared by a co-condensation reaction to create a mixed metal oxide system. A first mixture is formed by preparing ($C_{10}$-$C_{24}$)alkyl-tri($C_1$-$C_3$)alkylammonium halide surfactant micelles, which template the formation of the mixed metal oxide material in an alkali metal hydroxide-catalyzed condensation reaction of tetra($C_1$-$C_4$)alkylorthosilicates. The catalysts can be synthesized by first dissolving a ($C_{10}$-$C_{24}$)alkyl-tri($C_1$-$C_3$)alkylammonium halide (about 2-3 mmol) in about 400 mL to about 600 mL of approximately 15 mM aqueous alkali metal hydroxide. This solution can then be heated to about 70° C. to about 90° C., followed by a dropwise addition of a tetra($C_1$-$C_4$)alkylorthosilicate (about 20-24 mmol). White solids can be observed in the initially opaque emulsion in about 1-3 minutes after such addition with mixing. An alkaline earth metal oxide or hydroxide can then be added slowly to the stirring solution during the tetra($C_1$-$C_4$)alkylorthosilicate addition process. The reaction can then be vigorously stirred at about 70° C. to about 90° C. for about one to about four hours, followed by hot filtration of the as-synthesized catalyst product. The as-synthesized material can be washed with copious amounts of water and methanol and freeze dried. Surfactant removed catalysts can be obtained via calcination in air at about 100° C. to about 700° C. for about one hour to about twelve hours.

Various amounts of metal oxides can be employed, depending on the desired properties of the final catalyst. Catalysts of different properties can be prepared, for example, by using different amount of alkaline earth metal oxides in the above procedure, e.g., about 15-20 mmol of alkaline earth metal oxide, about 6-10 mmol of alkaline earth metal oxide, or about 2-5 mmol of alkaline earth metal oxide.

The biodiesel production process can be illustrated as below in Scheme 1.

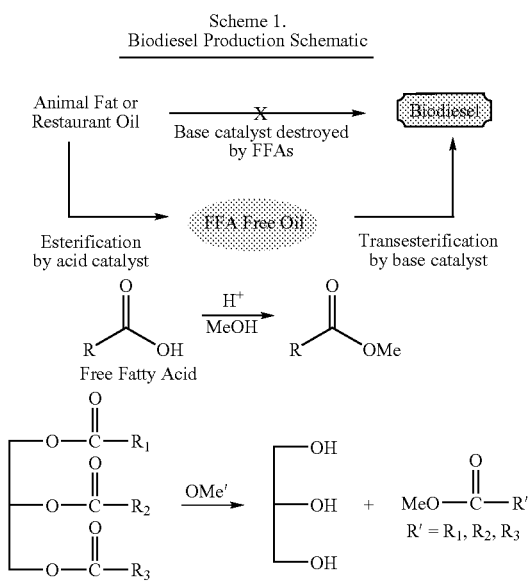

Scheme 1.
Biodiesel Production Schematic

For the transesterification of animal and vegetable oils with high free fatty acid content, the use of alkaline catalysts such as sodium hydroxide is undesirable because of the formation of relatively large amounts of soaps, leading to product loss and difficulty in the separation and purification of the biodiesel produced. The catalysts described herein avoid this problem because the catalysts are not negatively affected by the free fatty acids and in fact can be used to esterify such free fatty acids prior to transesterification of the animal or vegetable oils.

The porous silica-calcium oxide composite-based catalyst is more easily separated from a biodiesel reaction mixture than calcium oxide itself, so in turn the recyclability of the catalyst is significantly greater.

The following Example is intended to illustrate the above invention and should not be construed as to narrow its scope. One skilled in the art will readily recognize that the Example suggests many other ways in which the present invention could be practiced. It should be understood that many variations and modifications may be made while remaining within the scope of the invention.

EXAMPLES

General Experimental Details: Calcium oxide (CaO), magnesium oxide (MgO), barium oxide (BaO), and methanol were purchased from Fisher, tetraethylorthosilicate (TEOS) and n-cetyltrimethylammonium bromide (CTAB) were purchased from Aldrich. Degummed soybean oil and poultry fat were obtained from West Central. The Portland Cement is Holcim, Type 1, Type GU. All chemicals were used as received, without further purification. Nanopure water (18.1 MHz) prepared from a Barnstead E-pure water purification system was employed throughout.

Example 1

Preparation of Biodiesel Catalysts

Part I. Preparation of Mesoporous Calcium Silicate (MCS) Catalysts:

The preparation of mesoporous calcium silicate (MCS) catalysts involves a co-condensation reaction to create a mixed metal oxide system. Cetyltrimethylammonium bromide (CTAB) surfactant micelles template the formation of the mixed metal oxide material, in a NaOH-catalyzed condensation reaction of tetraethoxysilane (TEOS). The catalysts were synthesized by first dissolving n-cetyltrimethylammonium bromide (CTAB, 2.74 mmol) in 480 mL of 15 mM NaOH(aq). This solution was heated to 80° C., followed by a dropwise addition of tetraethylorthosilicate (TEOS, 22.4 mmol). White solids were observed in the initially opaque emulsion 90 seconds upon mixing. CaO was added slowly to the stirring solution during the TEOS addition process. The reaction was vigorously stirred at 80° C. for 2 hours, followed by hot filtration of the as-synthesized MCS product. The as-synthesized material was washed with copious amounts of water and methanol and freeze dried. Surfactant removed catalysts were obtained via calcination in air at 600° C. for 6 hours.

Three catalysts, with varying calcium oxide loading, were synthesized. MCS-1 catalyst was prepared by the above co-condensation method utilizing 17.8 mmol CaO, MCS-2 was prepared with 8.9 mmol CaO, and MCS-3 was prepared with 4.45 mmol CaO.

Part II. Preparation of Mesoporous Magnesium Silicate (MMS) Catalyst:

CTAB (1.0 g) was dissolved in nanopure water (465 mL) at room temperature. An aqueous solution of NaOH (2.0M, 3.5 mL) was added. The temperature was then increased to 80° C. TEOS (5.0 mL) was added dropwise, under stirring, followed by an aqueous suspension of Mg(OH)$_2$ just prepared by adding NH$_4$OH (30%, 7.5 mL) to an aqueous solution of MgCl$_2$.6H$_2$O (3.63 g, 5.5 mL). The system was kept under reflux for 2 hours. The solid was filtered out of the solution and washed with copious amount of water, then methanol, and dried overnight under vacuum. The as-synthesized material was then calcined at 500° C. (after a temperature increase of 4°/minute) for 10 hours.

Part III. Preparation of Mesoporous Barium Silicate (MBS) Catalyst:

CTAB (1.0 g) was dissolved in nanopure water (480 mL) at room temperature. An aqueous solution of NaOH (2.0M, 3.5 mL) was added. The temperature was then increased to 80° C. TEOS (5.0 mL) was added dropwise, under stirring, followed by a solid BaO (2.741 g). The system was kept under reflux for 2 hours. The solid was filtered out of the solution and washed with copious amount of water and methanol and dried overnight under vacuum. The as-synthesized material was then calcined at 550° C. (after a temperature increase of 2°/minute) for 6 hours.

Example 2

Evaluation of Biodiesel Catalysts

Part I. Soybean Oil Esterification:

Methanol (0.3 mol) was added to 100 mg of the calcined MCS catalyst, and the resulting solution was stirred 15-20 minutes at room temperature to uniformly disperse the catalyst. Utilizing the MCS-1 catalyst, the soybean oil (0.5 g) was added to the catalyst solution, and the reaction mixture was stirred under reflux at 80° C. for 26 hours. After 26 hours, the reaction mixture was filtered on a glass frit and rinsed with minimal methanol for transfer. The filtrate was evaporated under vacuum and analyzed by $^1$H NMR. The MCS-2 and MCS-3 catalysts required 48 hour reaction times with the above procedure to complete conversion, due to lower calcium oxide loading.

After further investigation, it was determined that a lower catalyst loading could likewise result in complete conversion to methyl esters. Merely 25 mg of the calcined MCS-1 catalyst can be employed to convert 0.5 mL of soybean oil to methyl esters in 12 mL of methanol, under the above conditions. Utilizing 10 mg of the calcined MCS-1 catalyst afforded 77% conversion of 0.5 mL soybean oil to methyl esters.

Part II. Poultry Fat Esterification:

Methanol (0.86 mol) was added to 350 mg of the calcined MCS catalyst, and like above, the resulting solution was stirred 15-20 minutes at room temperature to uniformly disperse the catalyst in a suspension. For esterification utilizing the MCS-1 catalyst, poultry fat (0.5 g) was added to the catalyst solution, and the reaction mixture was stirred under reflux at 80° C. for 26 hours. The reaction mixture was separated and analyzed as detailed above. Again, the MCS-2 and MCS-3 catalysts necessitated longer reaction times of 48 hours to complete conversion.

Part III. Yield Determination:

The esterification conversion percentage was determined via $^1$H NMR analysis. As mentioned above, the filtrate was evaporated, and an NMR spectrum was obtained in CDCl$_3$. The conversion was calculated by determining the ratio of methylene hydrogens, positioned at approximately 2.3 ppm, to methyl protons, positioned at approximately 3.6 ppm. As conversion proceeded, the characteristic peaks (~3.7-4.2 ppm) of the triglyceride backbone disappeared.

Part IV. Portland Cement and Hydrocal as Esterification Catalysts:

A similar procedure was utilized for Portland cement reactivity experiments. The reaction flask was charged with 500 mg Portland cement and 15 mL methanol, and this solution was allowed to stir 15-20 minutes to create an even suspension. Portland cement is denser than the MCS catalysts, so stirring was even more essential to ensure dispersion. Soybean oil (0.5 mL) was added and the reaction was stirred under reflux at 80° C. for 12 hours. When utilized for poultry fat esterification, 350 mg of catalyst was suspended in 35 mL methanol. This was likewise stirred to create a suspension, and 0.5 g poultry fat was added. The reaction was stirred under reflux at 80° C. for 26 hours. The catalyst was separated from the reaction mixture via centrifugation.

Hydrocal required the use of a higher amount of catalyst, 1 g in 15 mL methanol, to reach complete conversion. Once the Hydrocal was suspended, 0.5 mL soybean oil was added to the methanolic solution. The reaction was stirred under reflux at 80° C. for 30 hours. Like the Portland cement, the catalyst necessitated centrifugation for removal from the reaction mixture.

Part V. Results and Discussion:

Utilization of a heterogeneous solid acid-base catalyst for the synthesis of biodiesel can circumvent the catalyst separation problem and convert free fatty acids in crude FFA-containing feedstocks to biodiesel, so that the saponification during the transesterification reaction is prevented. To test the feasibility of using these mixed oxide solids as synergistic catalysts, the catalytic properties of the mesoporous calcium silicates (MCS) materials was examined for both the conversions of degummed soybean oil and poultry fat to biodiesel.

Figure 1:
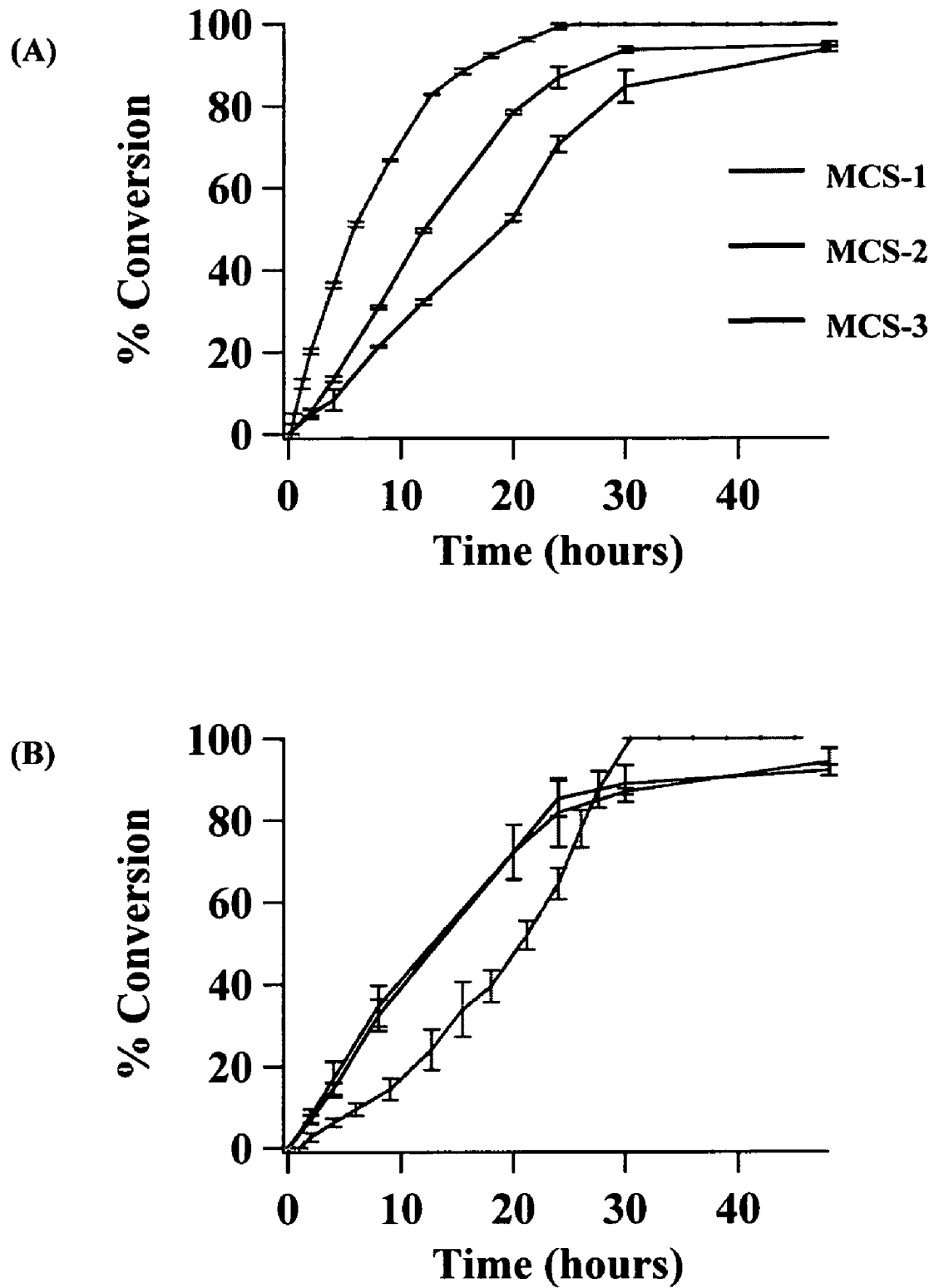
FIG. 1 illustrates the catalytic conversion of soybean oil (A) and poultry fat (B) into biodiesel by MCS catalysts. MCS-1 shows complete conversion within 24 hours for soybean oil, and 30 hours for poultry fat. MCS-2 and MCS-3 convert both soybean oil and poultry fat to biodiesel within 48 hours.

Catalytic activity: The MCS catalysts proved to be effective in the esterification of biomass feedstocks to biodiesel methyl esters. As mentioned above, current technologies require the use of pretreatment methods to remove FFAs from feedstocks prior to catalysis. The cooperative acid-base characteristics of the mixed oxide MCS catalysts eliminate the need for pretreatment measures. Both soybean oil and poultry fat sources can be utilized in esterification reactions without additional processes to remove FFAs. Shown in FIG. 1a is the catalytic activity of MCS-1, MCS-2, and MCS-3 for the esterification of soybean oil in methanol. Reaction completion was achieved within 24 hours for the MCS-1 catalyst (catalyst with the highest calcium oxide loading) at 80° C. The lower calcium oxide loaded MCS-2 and MCS-3 catalysts required 48 hours for quantitative conversion. FIG. 1b shows the catalytic activity of the three catalysts for the esterification of poultry fat in methanol. Reaction completion is reached within 30 hours at 80° C. for the MCS-1 catalyst. Again, due to the lower calcium oxide loading, the MCS-2 and MCS-3 catalysts required a longer reaction time of 48 hours to reach completion.

Figure 2:
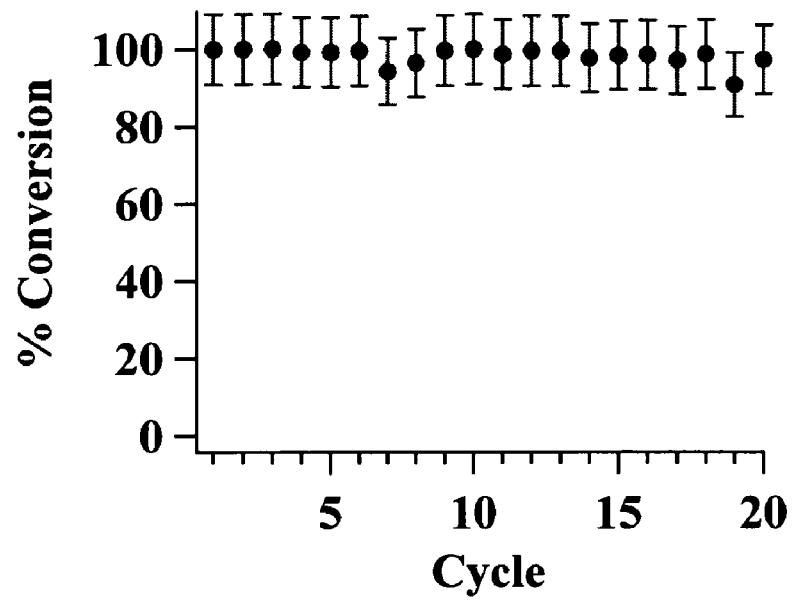
FIG. 2. Recyclability tests for the MCS-1 catalyst. Experiments show that the MCS-1 catalyst can facilitate the conversion of soybean oil to biodiesel 20 times with negligible yield loss, as seen in (A). The conversion of poultry fat to biodiesel can be seen for 8 successive reactions with minimal yield loss, as shown in (B).
Figure 2:
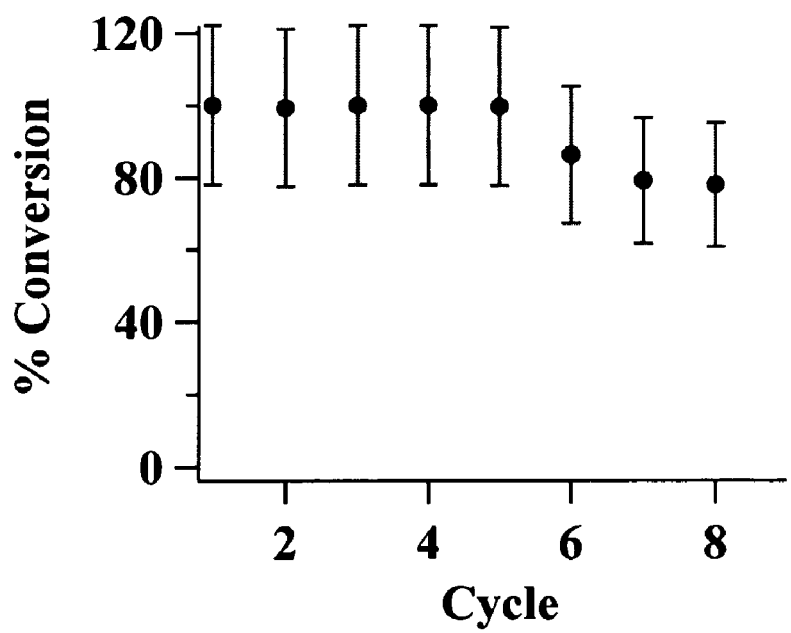

Recyclability: An important advantage of utilizing heterogeneous materials as catalysts is the possibility of recycling these solids. In this work, catalyst recycling was achieved by simple filtration of the mixture at the end of the reaction. The recovered catalyst was used again under the same reaction conditions. The catalyst MCS-1 was reused up to 20 times for soybean oil transesterification reaction (FIG. 2a) and up to 8 times for poultry fat transesterification reaction as shown in FIG. 2b. Remarkably, there was no significant loss of activity in each case. Initial results show also that the MCS-2 and MCS-3 catalysts can be reused up to 5 times for both poultry fat and soybean oil transesterification reactions with negligible loss of activity. The excellent recyclability of these catalysts indicates that they are stable and there is no leaching of calcium. This is most likely due to the unique structure obtained via co-condensation reaction, which yields a very stable and structurally homogenous calcium silicate mixed oxide material.

As summarized in Table 1, the catalytic performances and the recyclability of the MCS materials described herein are better in comparison with those of many other solid metal oxide catalysts. For example, calcium oxide (CaO) and calcium hydroxide (Ca(OH)$_2$) are efficient catalysts for the transesterification reaction of soybean oil. However, traces of free fatty acids in the raw material would allow for saponification of biodiesel when employing these strong bases. Moreover, CaO and Ca(OH)$_2$ are quite soluable in methanol (*Bioresource Technology* 1999, 70, (3), 249-253). This behavior prevents these two compounds from being reused and also would require neutralization of the products with hydrochloric acid and extensive washes with water.

TABLE 1

Reactivity and Recyclability results of MCS catalysts, and comparisons to Portland Cement.

| | Soybean Oil | | Poultry Fat | |
|---|---|---|---|---|
| Catalyst | Esterification Conversion (%) | Recyclability (Cycles) | Esterification Conversion (%) | Recyclability (Cycles) |
| MCS-1 | 100[a] | 20 | 100[e] | 8 |
| MCS-2 | 95[b] | 5 | 93[f] | 5 |
| MCS-3 | 94[b] | 5 | 94[f] | 5 |
| Hydrocal | 100[c] | 1 | N/A | N/A |
| Portland Cement | 97[d] | 1 | 7[e] | 1 |

[a]100 mg catalyst converted 0.5 mL soybean oil in 26 hours at 80° C. in 12 mL MeOH;
[b]100 mg catalyst converted 0.5 mL soybean oil in 48 hours at 80° C. in 12 mL MeOH;
[c]1 g catalyst converted 0.5 mL soybean oil in 30 hours at 80° C. in 15 mL MeOH;
[d]500 mg catalyst converted 0.5 mL soybean oil in 12 hours at 80° C. in 15 mL MeOH;
[e]350 mg catalyst converted 0.5 g poultry fat in 26 hours at 80° C. in 35 mL MeOH;
[f]350 mg catalyst converted 0.5 g poultry fat in 48 hours at 80° C. in 35 mL MeOH.

The catalytic performance of magnesium oxide (MgO) has been evaluated and is capable of converting soybean oil to biodiesel. Unlike calcium oxide, the rate of the reaction is much slower, and it takes 125 hours to reach 98.3% yield. Magnesium oxide, like calcium oxide, is quite soluble in methanol. Therefore, it cannot be recycled and it also would require purification of biodiesel by neutralization with acid and washes with water.

In addition, the results herein indicate that CaO-fumed silica is an effective catalyst for converting soybean oil to biodiesel. Quantitative conversion was observed in 6 hours. However, the attempt to recycle and reuse this catalyst resulted in a significant loss of reactivity. After a few cycles, the conversion is reduced to below 30%. This result suggests that CaO gradually dissolved in methanolic solution, which caused the aforementioned saponification and neutralization issues. The catalytic performances of these alkaline earth metal-containing materials are summarized in Table 2.

TABLE 2

Reactivity results for some other alkaline earth metal containing catalysts.

| Catalyst | Yield in methyl esters (%) | Reaction Time (hours) |
|---|---|---|
| Bulk CaO | 100[a] | 2 h |
| Bulk Ca(OH)$_2$ | 100[a] | 0.5 h |
| CaO-fumed silica | 100[b] | 6 h |
| Bulk MgO | 98.3[c] | 125 h |
| Mg-MSN | 100[b] | 125 h |
| Ba-MSN | 56[b] | 48 h |

[a]300 mg converted 1.5 mL soybean oil at 80° C. in 36 mL MeOH;
[b]100 mg converted 0.5 mL soybean oil at 80° C. in 12 mL MeOH;
[c]35 mg converted 0.5 mL soybean oil at 80° C. in 12 mL MeOH.

Structural Analysis

Nitrogen Adsorption Analysis: The mesoporous structures of the MCS materials were determined by nitrogen adsorption-desorption surface analysis. The surface area of the MCS catalysts decreases with increasing calcium oxide loading, as shown in Table 3.

TABLE 3

Nitrogen sorption analysis of the MCS catalysts. The surface area is shown to decrease as the calcium oxide loading increases.

| Catalyst | BET Surface Area (m$^2$/g) | BJH Pore Size Distribution (nm) |
|---|---|---|
| MCS-1 | 262 | 9.2 |
| MCS-2 | 443 | <2 |
| MCS-3 | 890 | 2.5 |
| Hydrocal | 1 | <2 |
| Portland Cement | 1 | <2 |

Figure 3:
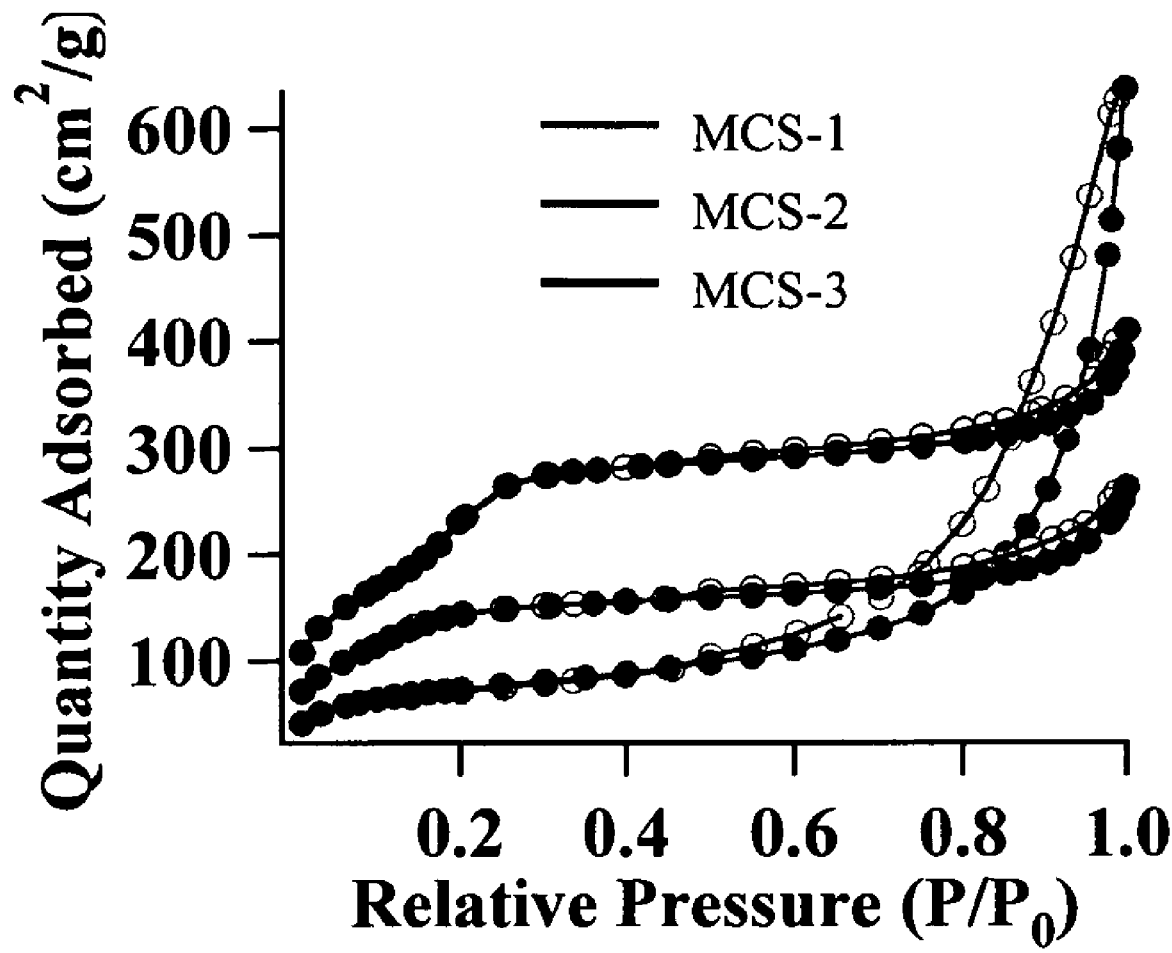
FIG. 3. Nitrogen sorption analysis: the surface area is shown to decrease with increasing calcium oxide loading.

Table 3 illustrates that all three MSC catalysts have higher surface areas than both Portland Cement and Hydrocal. As is evident from the BET isotherms (FIG. 3) of the three catalysts, the hysteresis is shown to increase in size with higher calcium oxide content, possibly indicating the formation of micropores, or interconnecting pores with higher calcium oxide loading.

Figure 4:
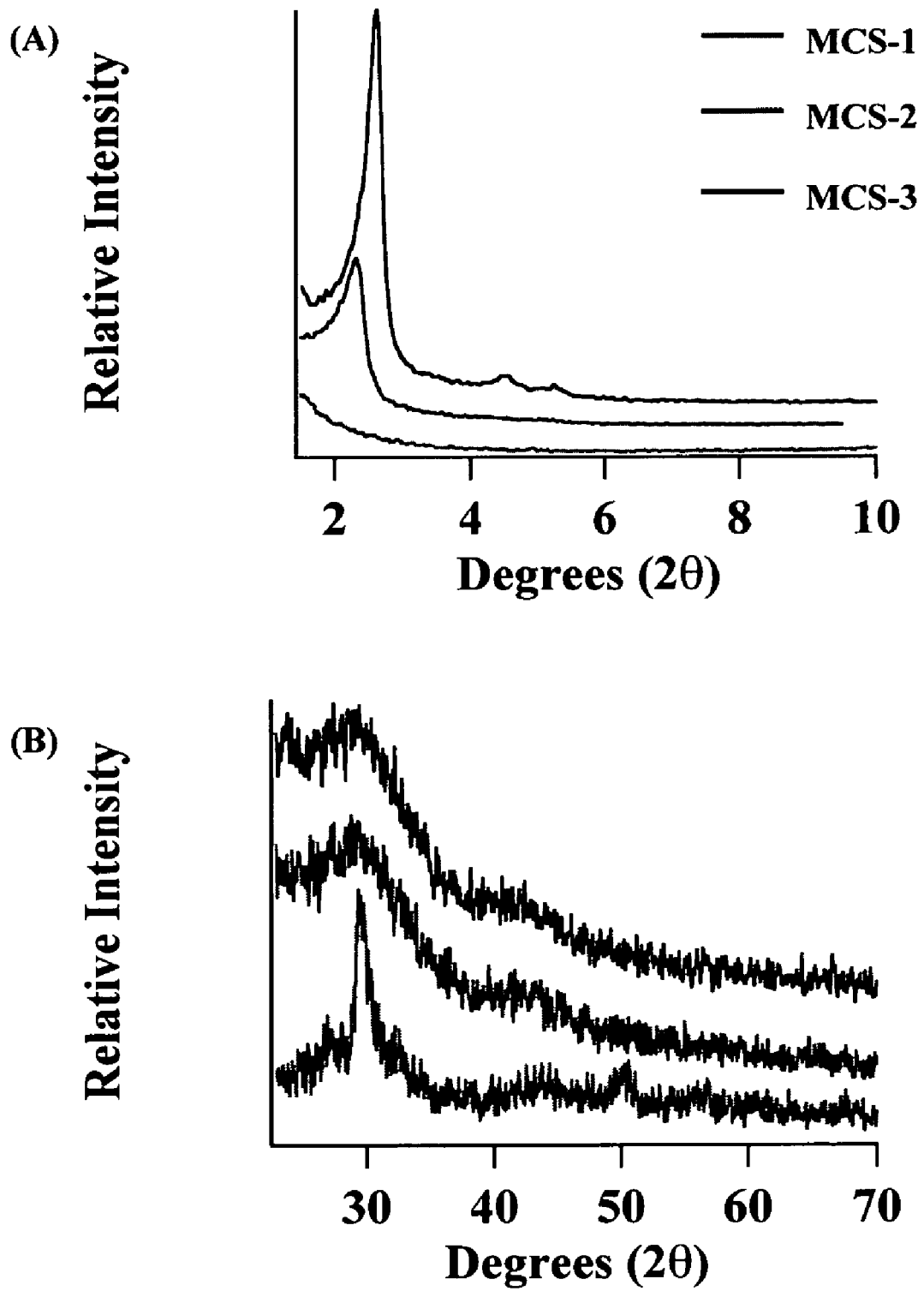
FIG. 4. Powder X-ray diffraction patterns of the MCS catalysts. The lower calcium oxide loaded samples show higher order, as evident in (A). The MCS-1 catalyst demonstrates peaks at high angles, as seen in (B).

Powder X-Ray Diffraction: Low angle powder X-Ray Diffraction spectra were obtained for the three MSC catalysts to measure the degree of order present in the materials. As can be seen in FIG. 4a, the order decreases with the loading of calcium oxide. The MCS-3 catalyst, with the lowest calcium oxide loading, possesses $d_{100}$, $d_{110}$, and $d_{200}$ peaks characteristic of hexagonally ordered MCM-41 materials. The absence of these peaks at higher calcium oxide loading confirms the electron microscopy results, which indicate an increase in disorder with increasing calcium oxide loading.

The X-Ray diffraction pattern at higher angles, FIG. 4b, showed the characteristic peaks of amorphous silica (~30 degrees 2θ). The MCS-2 and MCS-3 catalysts showed no further peaks; however, the MCS-1 catalyst possesses further peaks around 30°, 43°, and 50° 2θ. The high angle XRD analysis surprisingly showed the absence of peaks characteristic to calcium oxide. These results may indicate that there are not discrete crystalline calcium oxide sites present, but a structure in which calcium is incorporated into the matrix of the material.

Figure 5:
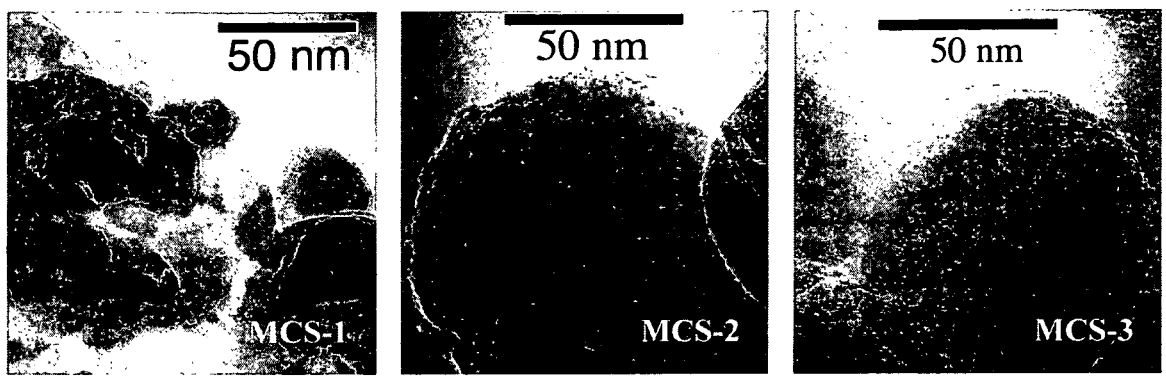
FIG. 5. TEM spectra of MCS-1, MCS-2, and MCS-3. An amorphous, disordered structure is observed with the highest calcium oxide loaded MCS-1 sample, and more spherical morphologies with wormhole pores are demonstrated for the lower calcium oxide loaded samples.
Figure 6:
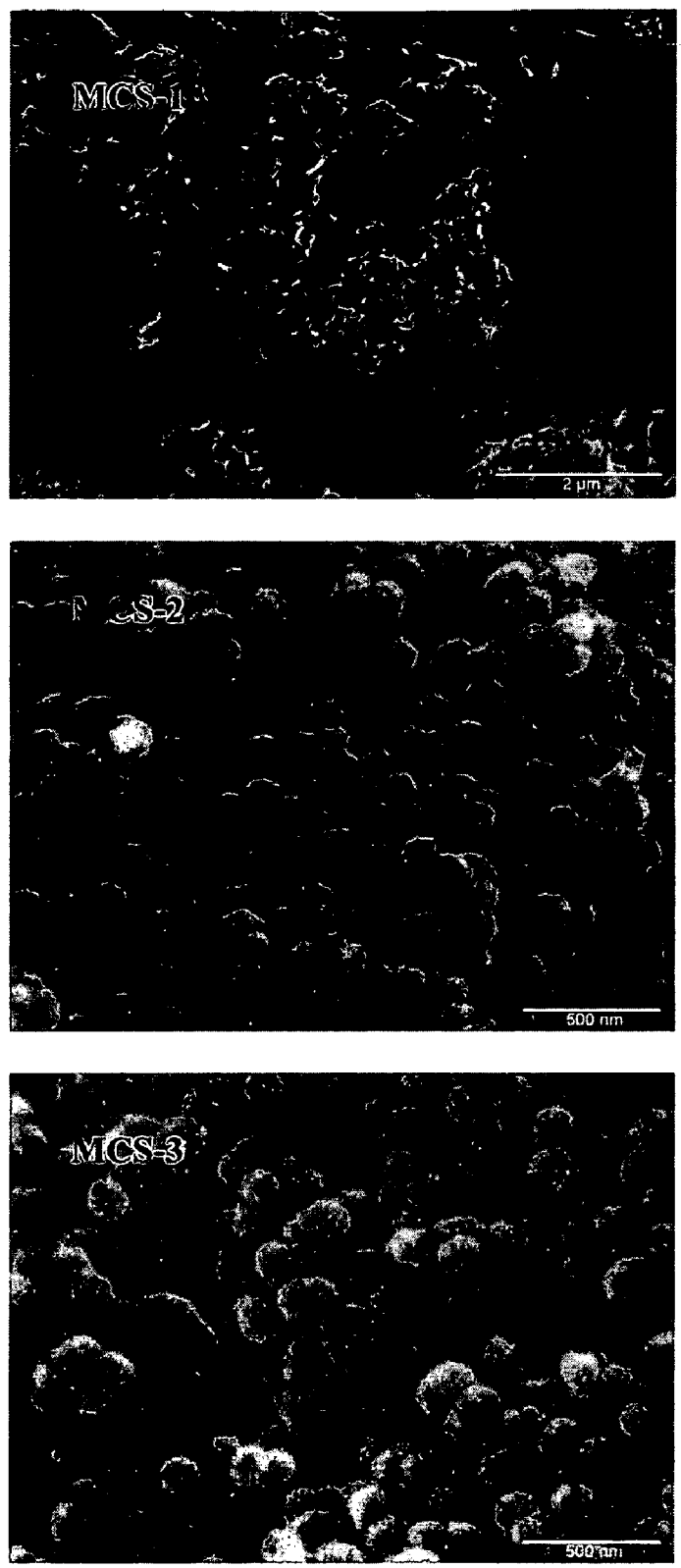
FIG. 6. Scanning electron micrographs show the increase in monodispersity as the calcium oxide content is lowered. The structure of MCS-1 appears sponge-like and amorphous, whereas the MCS-2 and MCS-3 catalysts are semi-spherical morphologies which are fairly uniform in size.

Electron Microscopy: Scanning electron and transmission electron microscopy (SEM and TEM, respectively) were performed on the MCS catalysts to determine the morphology and give more information regarding the porous structure of the catalysts. The TEM analysis supports the nitrogen adsorption and XRD results in that the highest loaded catalyst appears to possess a disordered pore structure, while the lower loaded catalysts appear to have wormhole porous structures, as can be seen in FIG. 5. The SEM spectra, FIG. 6, establish that the highest calcium oxide loaded MCS-1 yielded a sponge-like amorphous structure, whereas the lower loaded samples exhibited more ordered, spherical morphologies.

The catalysts are made from commercially available sources and provide a means to complete the esterification of biomass feedstocks without the use of harsh chemicals, or catalyst neutralization. The biodiesel methyl ester product is desirable in that it is environmentally friendly and can be synthesized from bio-renewable feedstock.

Figure 7:
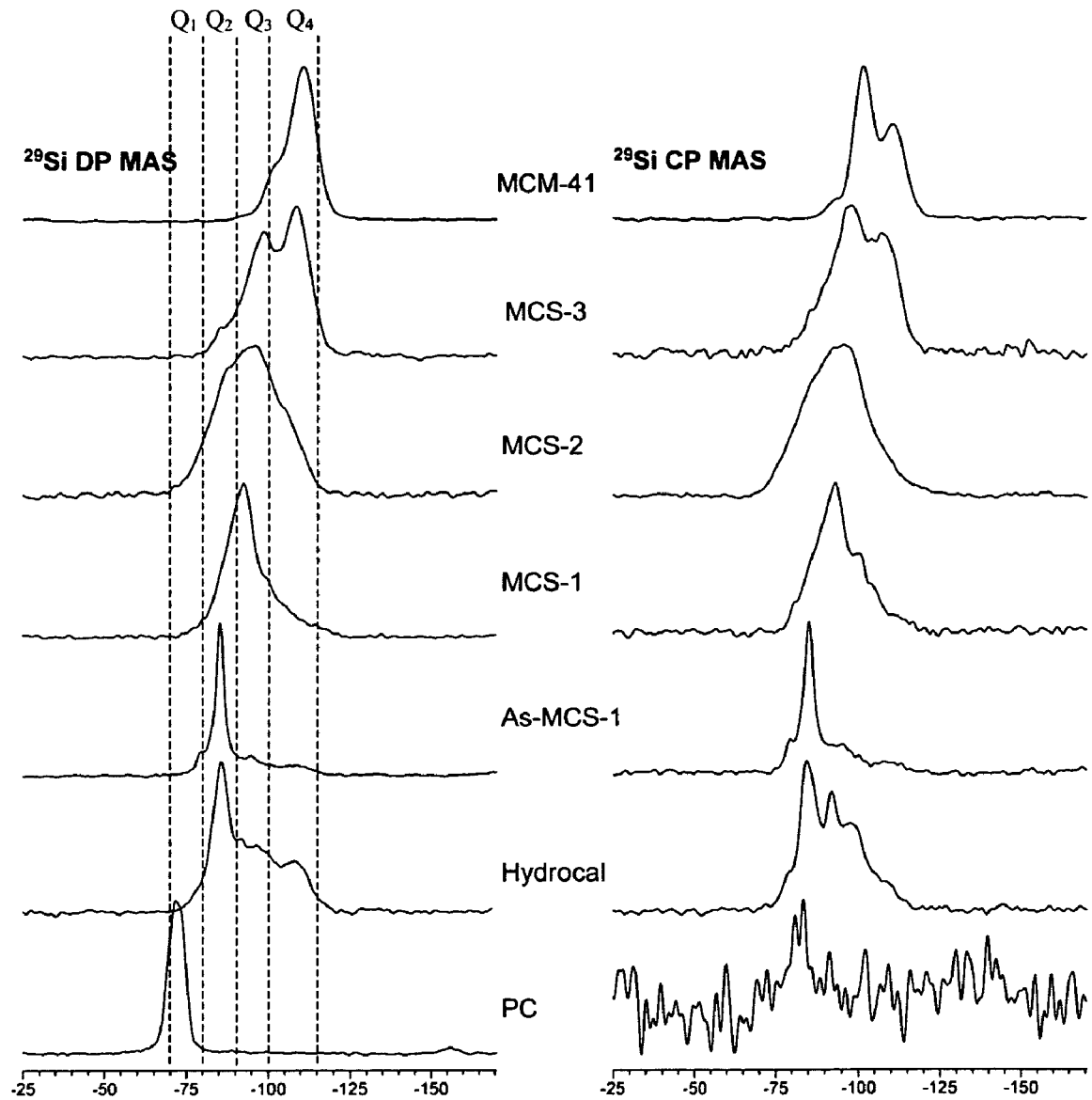
FIG. 7. $^{29}$Si DPMAS (left column) and $^1$H-$^{29}$Si CPMAS (right column) spectra of MCM-41, calcinated MCS-1, 2, and 3, as synthesized MCS-1, Hydrocal, and Portland cement.

Solid State NMR Results. FIG. 7 illustrates the $^{29}$Si DPMAS and $^1$H-$^{29}$Si CPMAS spectra of MCM-41, calcined MCS catalysts (denoted as MCS-1, MCS-2, MCS-3, respectively), as-synthesized MCS-1 (denoted as As-MCS-1), Hydrocal, and Portland cement (PC). The corresponding spectra of Hydrocal (HC, not shown) are identical to those of the Portland cement. The fact that the DP- and CP-MAS NMR spectra of the MCS materials are similar indicated that there is no bulk silica present in these mixed oxide materials.

The Ca/Si ratios in these samples are listed in Table 4. They were estimated using two different methods: 1) Spin counting: for each sample the total integrated intensity of $^{29}$Si DPMAS spectrum was compared with a reference (using all usual precautions in such measurements); and 2) the $^{29}$Si DPMAS spectra were deconvoluted into peaks representing separate $Q^n$ groups; the Ca/Si ratios were then calculated in similar manner as Si/Al ratio in zeolites.

TABLE 4

| Ca/Si ratios calculated form $^{29}$Si spin counting results. | | | | | | |
|---|---|---|---|---|---|---|
| Sample | MCS-3 | MCS-2 | MCS-1 | As-MCS-1 | PC | HC |
| Spin counting | 0.2 | 1.0 | 1.7 | 1.8 | | |
| Deconvolution | 0.1 | 1.0 | 1.7 | 1.6 | 2.0 | 2.0 |

In contrast to other literature-reported mixed oxides, where the different oxides are usually distributed in domains and separated from each other, the values of the MCS catalysts described herein obtained by spin counting and deconvolution methods are in good agreement, which suggests that calcium forms an intimate and homogeneous mixture with silicon. In fact, the calcium silicate catalyst contains a structural unit that is similar to a crystalline calcium silicate, 1.4 nm tobermorite (*Cement and Concrete Research* 2004, 34, (9), 1499-1519), which is a composite layer composed of a distorted central Ca—O sheet that is ribbed on either side with single dreierketten, i.e., silicate chains that repeat at intervals of three silicate tetrahedra as depicted in FIGS. 8*a* and *b*. Unlike other calcium silicate hydrate gels, where water and calcium cations exist between layers of 1.4 nm tobermorites (FIGS. 8*b* and *c*), the bridging silicate tetrahedra ($Q^2$ Silicons) of the MSC catalyst material are connected and formed $Q^3$-type Si atoms (FIG. 8*d*) (see *J. Physical Chemistry B* 2004, 108, (40), 15,494-15,502). The overall material exhibits a spherical particle morphology with wormhole-like mesopores. As determined by the spin counting of $^{29}$Si NMR spectroscopy, this unique structure gives rise to a high Ca/Si ratio of 1.8, which is very different from the value (0.83) of tobermorite in common calcium silicate hydrate gels (*Cement and Concrete Research* 2004, 34, (9), 1499-1519). The observed high Ca/Si ratio further supports a "Charge Difference" hypothesis (see *Korean Journal of Chemical Engineering* 1997, 14, (3), 192-197) that the enhanced Lewis acidity can be attributed to the replacement of Ca atoms with silicon atoms at sites with high coordination numbers of oxygen atoms.

Portland Cement and Hydrocal as Esterification Catalysts: Through structural analysis, it was determined that the MSC catalysts are similar in some respects to calcium silicate hydrates. This investigation led to conducting catalytic comparisons with Portland cement and other calcium silicates hydrates. Commercially available Portland cement showed catalytic reactivity for the conversion of soybean oil to biodiesel methyl esters. Conversion of 0.5 mL soybean oil (in 15 mL methanol) could be completed within 12 hours at 80° C. when utilizing 500 mg of Portland cement. The Portland cement thus proved to be a viable catalyst for soybean oil esterification. Catalyst recovery however proved to be more difficult than with MCS catalysts, so the Portland cement was not able to be recycled for further reactions.

Though successful as a catalyst for the esterification of soybean oil, Portland cement shows minimal catalytic reactivity for the conversion of poultry fat to biodiesel methyl esters. When charged with 350 mg of Portland cement catalyst, conversion of 0.5 g poultry fat (in 35 mL methanol) only reached 7.3% within 26 hours. The catalyst gummed up and was thus difficult to recover and/or recycle.

Hydrocal also proved to be an active catalyst for the esterification of soybean oil to biodiesel. In 30 hours, 1 g of Hydrocal facilitated the conversion of 0.5 mL soybean oil (in 15 mL methanol). Hydrocal, like Portland Cement, was difficult to recover and thus was not able to be reused in successive reactions.

Conclusions: Acid-base mesoporous calcium oxide-silica nanoparticles have been prepared and have been shown to catalyze the esterification of fatty acids to methyl esters. The catalysts have proven to be effective in the conversion of both soybean oil and the higher FFA containing poultry fat biomass feedstocks to biodiesel methyl esters. The catalysts can be used for successive reactions, without neutralization steps, and with minimal yield loss. The MCS catalysts, which facilitate the conversion of bio-renewable feedstocks to biodiesel methyl esters, can be easily recycled, thus proving to be both environmentally and economically friendly.

Hydrocal, Portland cement, and other calcium silicate hydrates prove to be efficient catalysts for the esterification of soybean oil. However, due to the inability to recover the catalyst, they offer limited use. Portland cement is unable to catalyze the esterification of poultry fat to biodiesel without gumming up the catalyst.

Thus, a new cooperative catalytic system comprised of a series of bifunctional mesoporous mixed oxide materials has been developed. These materials contain both Lewis acidic and Lewis basic sites for the synthesis of biodiesel from various free fatty acid (FFA)-containing oil feedstocks, such as animal fats and restaurant waste oils. It has been demonstrated that the acid and base functionalities can cooperatively catalyze both the esterification of FFAs and the transesterification of oils with short-chain alcohols (e.g. methanol and ethanol) to form alkyl esters (biodiesel). The reactivity and recyclability of these heterogeneous solid catalysts have been investigated. In the case of soybean oil, the catalyst can be recycled 20 times without any decrease in reactivity. It is envisioned that that these nanoporous mixed oxides can serve as new selective catalysts for many other important reactions involving carbonyl activation.

Example 3

MCS/Metal Oxide Blend Catalysts

Part 1. Catalytic Performances of a Solid Blend of CaO/MCS Catalysts.

Figure 9:
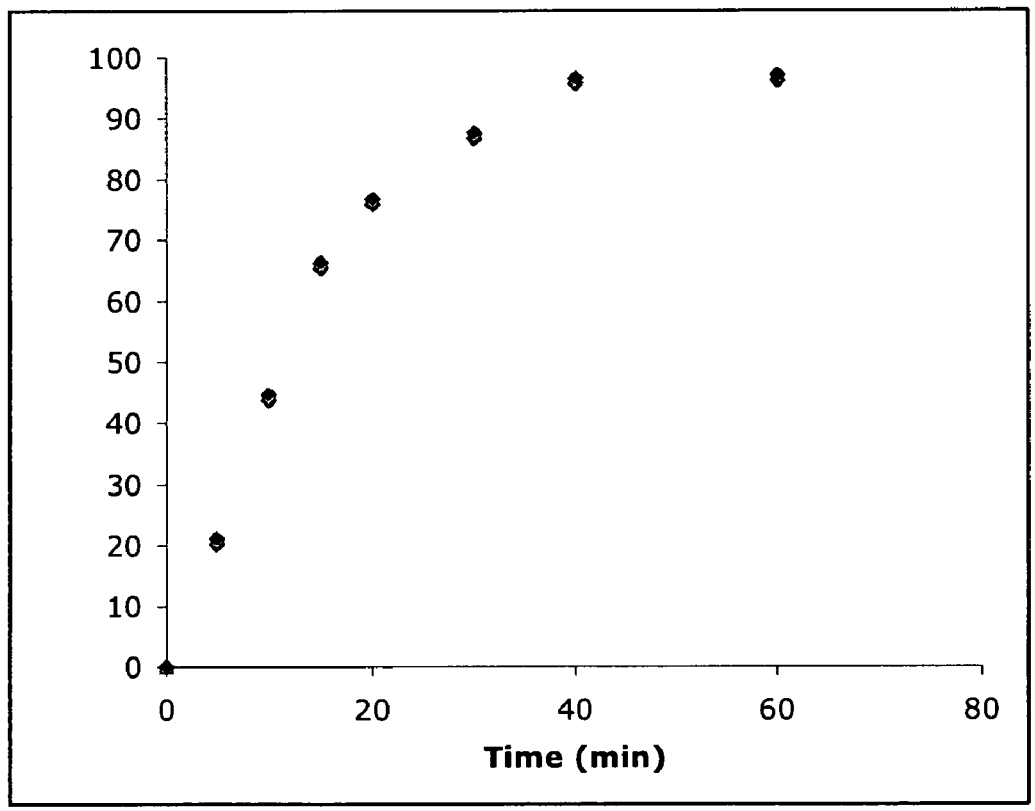
FIG. 9. A plot of yield versus reaction time for a solid blend catalyst of CaO/MCS-1 (first run) for the conversion of soybean oil to biodiesel.

Solid Blend of CaO with MCS-1: Methanol (0.3 mol) was added to a solid blend consisting of 50 mg of CaO and 50 mg of calcined MCS-1 catalyst. The resulting mixture was stirred at 80° C. to uniformly disperse the catalyst. After stirring for 30 minutes, soybean oil (2.5 mL) was introduced and the reaction mixture was stirred at 80° C. The complete conversion of soybean oil to biodiesel took 40 minutes as depicted in FIG. 9. The crude product mixture was filtered through a glass-fritted funnel. The product-containing filtrate was evaporated under vacuum to remove methanol. The yield of methyl esters (biodiesel) was analyzed by $^1$H NMR.

Figure 10:
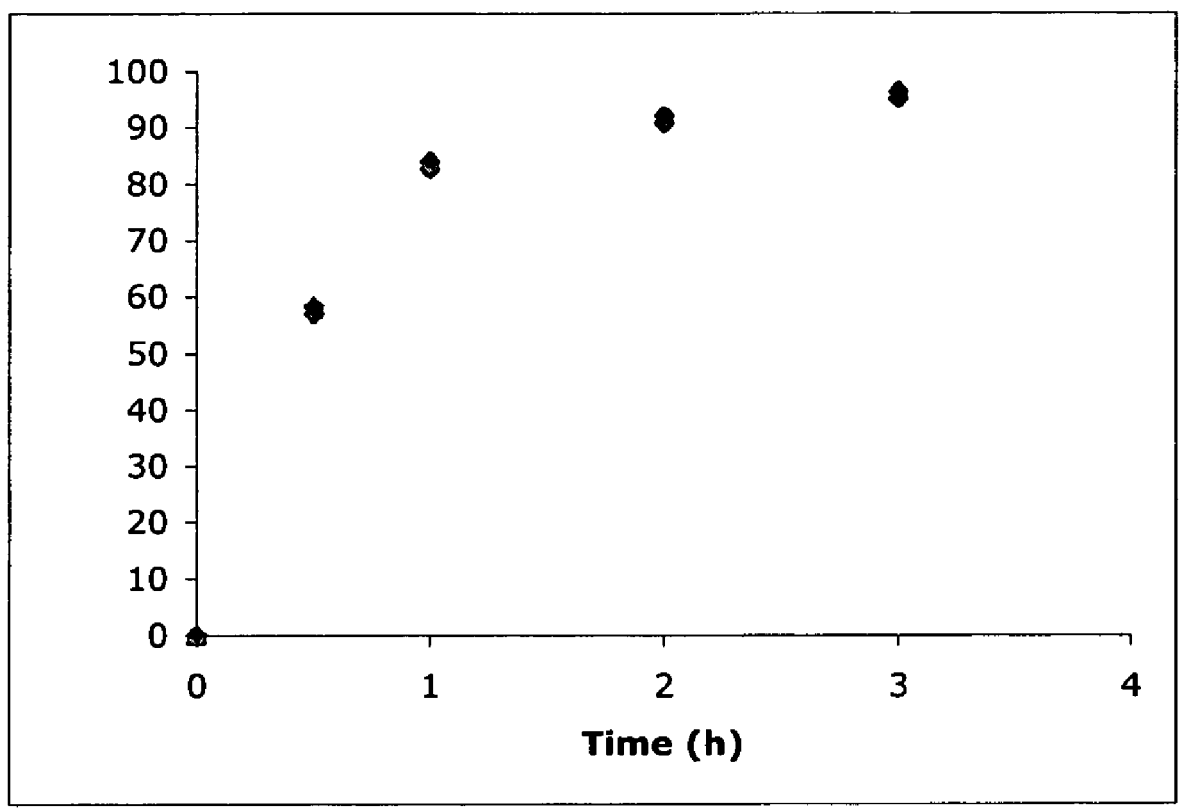
FIG. 10. A plot of yield versus reaction time for a solid blend catalyst of CaO/MCS-2 (first run) for the conversion of soybean oil to biodiesel.

Solid Blend of CaO with MCS-2: By following the aforementioned procedures, a solid blend of CaO (50 mg) and calcined MCS-2 (50 mg) was found to be able to catalytically convert soybean oil (2.5 mL) to biodiesel within 2 hours as shown in FIG. 10.

Recyclability: The catalysts were recycled by simple filtration of the reaction mixture upon the completion of the transesterification reaction. The recovered catalyst was reused without any purification under the same reaction conditions, with the exception of a longer reaction time. For the blend of CaO/MCS-2, the complete conversion of soybean oil to biodiesel took 2 hours for the first run and 6 hours for the subsequent runs (Table 5). This catalyst was reused up to 7 times for soybean oil transesterification reaction with no loss of reactivity after the second run. For the blend of CaO/MCS-1, the complete conversion of soybean oil to biodiesel took 40 minutes for the first run and 6 hours for additional runs (Table 6).

TABLE 5

Recyclability of the blend CaO/MCS-2 catalyst.

| Run | Yield (%) | |
| --- | --- | --- |
| | 2 h | 6 h |
| 1 | 92.1% | 96.5% |
| 2 | 41.1% | 92.7% |
| 3 | 50.5% | 92.5% |
| 4 | 37.8% | 93.9% |
| 5 | 10.4% | 93.5% |
| 6 | 13.2% | 94.6% |
| 7 and on | similar reactivity | |

TABLE 6

Recyclability of the blend CaO/MCS-1 catalyst.

| Run | Time (h) | Yield (%) |
| --- | --- | --- |
| 1 | 0.67 | 93.4 |
| 2 | 7 | 94.1 |
| 3 | 12 | 92.5 |

Part 2. Catalytic Performances of the Calcined CaO/MCS Catalysts.

The mixture of as-synthesized MCS catalysts and CaO prior to calcination also resulted in an active catalyst for transesterification of oils to biodiesel. The dry powders were blended in a 1 MCS:1 CaO weight ratio and then calcined at 600° C. for 6 hours. The reactivity and recyclability of the resulting catalyst was evaluated according to the conditions stated above for the blend CaO/MCS catalysts.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A recyclable esterification or transesterification catalyst comprising one or more porous particles that have a composite matrix of mesoporous silicate and alkaline earth metal oxide moieties;
    wherein the catalyst has a silicon to alkaline earth metal ratio of about 0.1 to 1;
    the catalyst contains both inorganic acidic and inorganic basic sites; and the catalyst has a surface area of greater than about 50 m$^2$ per gram.

2. The catalyst of claim 1 wherein the alkaline earth metal is magnesium, calcium, or barium.

3. The catalyst of claim 1 wherein the pores of the particle are about 1 nm in diameter to about 20 nm in diameter.

4. The catalyst of claim 1 wherein the alkaline earth metal is calcium and bridging silicate tetrahedra are connected to form Q$^3$-type silicon atom geometry, and the catalyst exhibits spherical or sheet-like particle morphology with worm-like or channel-like mesopores.

5. The catalyst of claim 1 further comprising metal oxide particles, wherein the metal oxide particles are magnesium oxide, calcium oxide, barium oxide, or a combination thereof.

6. A method for transesterifying an ester to provide a ($C_1$-$C_4$)alkyl ester comprising: combining the ester, a ($C_1$-$C_4$) alcohol, and the catalyst of claim 1 under conditions wherein the catalyst catalyzes the formation of the ($C_1$-$C_4$)alkyl ester of the acid portion of the ester and the corresponding free alcohol of the ester.

7. A method for preparing fatty acid ($C_1$-$C_4$)alkyl esters from a feedstock that comprises one or more fatty acid glycerol esters and one or more fatty acids comprising: combining the feedstock, a ($C_1$-$C_4$)alcohol, and the catalyst of claim 1 under conditions wherein the catalyst catalyzes the formation of the corresponding fatty acid ($C_1$-$C_4$)alkyl esters.

8. A method for producing a fatty acid ($C_1$-$C_4$)alkyl ester comprising: combining a glyceride-containing vegetable or animal oil, a ($C_1$-$C_4$)alcohol, and the catalyst of claim 1 under conditions wherein the catalyst catalyzes formation of the corresponding fatty acid ($C_1$-$C_4$)alkyl ester and glycerol.

9. A method for preparing a fatty acid ($C_1$-$C_4$)alkyl ester from a fatty acid comprising: combining a fatty acid, a ($C_1$-$C_4$)alcohol, and the catalyst of claim 1 under conditions wherein the mesoporous silicate catalyzes formation of the corresponding fatty acid ($C_1$-$C_4$)alkyl ester.

10. A method for producing methyl soyate comprising: combining soybean oil, methanol, and the catalyst of claim 1 under conditions wherein the mesoporous silicate catalyzes formation of glycerol and the methyl soyate.

11. The method of any one of claims 6-9 wherein the ester comprises a $C_8$-$C_{22}$ fatty acid ester.

12. The method of any one of claims 6-9 wherein the ester is a mono-, di-, or tri-ester of glycerol.

13. The method of any one of claims 6-9 wherein the ($C_1$-$C_4$)alcohol is methanol or ethanol.

14. The method of any one of claims 6-9 wherein the formation of the ester is carried out at a temperature of less than about 100° C.

15. The method of any one of claims 6-10 wherein the formation of the ester is carried out without added solvent.

16. A method for preparing a mesoporous silicate alkaline earth metal oxide composite-based catalyst comprising:
   a) combining a ($C_8$-$C_{22}$)alkyl-tri($C_1$-$C_3$)alkylammonium halide, water, and a base, in the absence of an organic solvent, to form a first mixture;
   b) heating the first mixture;
   c) combining the first mixture with a tetra($C_1$-$C_4$)orthosilicate and an alkali metal oxide or alkali metal hydroxide, to provide the catalyst in a second mixture;
   d) recovering the mesoporous catalyst from the second mixture; and
   e) heating the catalyst to about 100° C. to about 600° C.; to provide a mesoporous silicate alkaline earth metal oxide composite-based catalyst that has a composite matrix of mesoporous silicate and alkaline earth metal oxide moieties; wherein the catalyst has a silicon to alkaline earth metal ratio of about 0.1 to 1; and the catalyst contains both inorganic acidic and inorganic basic sites and has a surface area of greater than about 50 $m^2$ per gram.

17. The method of claim 16 wherein the alkaline earth metal is calcium, and the base is an alkali metal hydroxide.

18. The method of claim 16 wherein the catalyst is combined with a metal oxide particle, wherein the metal oxide particle comprises magnesium oxide, calcium oxide, barium oxide, or a combination thereof.

* * * * *